US011176258B2

(12) United States Patent
    Fourman

(10) Patent No.: US 11,176,258 B2
(45) Date of Patent: *Nov. 16, 2021

(54) CONTENT DELIVERY SYSTEM AND METHOD OF DELIVERING

(71) Applicant: Gaiasoft IP Limited, London (GB)

(72) Inventor: Clive Morel Fourman, London (GB)

(73) Assignee: Gaiasoft IP Limited, London (GB)

( * ) Notice: Subject to any disclaimer, the term of this patent is extended or adjusted under 35 U.S.C. 154(b) by 0 days.

This patent is subject to a terminal disclaimer.

(21) Appl. No.: 17/117,946

(22) Filed: Dec. 10, 2020

(65) Prior Publication Data

US 2021/0165889 A1   Jun. 3, 2021

Related U.S. Application Data

(63) Continuation of application No. 13/706,201, filed on Dec. 5, 2012, now Pat. No. 10,878,107, which is a
(Continued)

(51) Int. Cl.
    *G06F 21/60* (2013.01)
    *H04L 29/08* (2006.01)
    *G06F 16/9535* (2019.01)
    *G16H 10/60* (2018.01)
    *G06F 19/00* (2018.01)
    *H04L 29/06* (2006.01)

(52) U.S. Cl.
    CPC .......... *G06F 21/60* (2013.01); *G06F 16/9535* (2019.01); *G06F 19/00* (2013.01); *G16H 10/60* (2018.01); *H04L 67/306* (2013.01); *H04L 63/102* (2013.01); *H04L 67/28* (2013.01)

(58) Field of Classification Search
    CPC ..... G06F 19/322; G06F 21/60; H04L 63/102; H04L 67/28; H04L 67/306
    See application file for complete search history.

(56) References Cited

U.S. PATENT DOCUMENTS 5,901,287 A    5/1999 Bull et al.
7,894,448 B1   2/2011 Lillibridge et al.
(Continued)

OTHER PUBLICATIONS

Related U.S. Appl. No. 12/594,864, filed Oct. 30, 2009.

*Primary Examiner* — Hitesh Patel
(74) *Attorney, Agent, or Firm* — Finnegan, Henderson, Farabow, Garrett & Dunner, LLP

(57) ABSTRACT

A content delivery system (100) comprises a trusted holder of profile data (200) arranged to store information concerning a conscious entity, a content delivery requirement entity (210), a content intermediary entity (226); and a source of content (232). The trusted holder of profile data (200) is arranged to issue (230) profile reference data to the content delivery requirement entity in response to a request (222) therefrom, and to communicate (224) the profile reference data and at least part of the stored information concerning the conscious entity to the content intermediary entity (226), the request for content provision (222) being capable of identifying the conscious entity to the trusted holder of profile data. The content intermediary entity (226) is arranged to source, when in use, relevant content from the source of content (232) using the at least part of the stored information concerning the conscious entity.

51 Claims, 3 Drawing Sheets

Related U.S. Application Data continuation of application No. 12/594,864, filed as application No. PCT/GB2008/050246 on Apr. 7, 2008, now abandoned.

(60) Provisional application No. 60/922,085, filed on Apr. 6, 2007.

(56) References Cited

U.S. PATENT DOCUMENTS

| | | |
|---|---|---|
| 8,327,128 B1 | 12/2012 | Prince et al. |
| 2001/0054155 A1 | 12/2001 | Hagan et al. |
| 2003/0059750 A1 | 3/2003 | Bindler et al. |
| 2005/0076248 A1* | 4/2005 | Cahill ................ G06Q 20/0855 726/19 |
| 2006/0020508 A1 | 1/2006 | Gorti et al. |
| 2006/0184997 A1* | 8/2006 | La Rotonda .......... H04L 67/306 726/2 |
| 2007/0112762 A1 | 5/2007 | Brubaker |
| 2010/0094806 A1 | 4/2010 | Apostolides et al. |

* cited by examiner

CONTENT DELIVERY SYSTEM AND METHOD OF DELIVERING

RELATED APPLICATIONS

This application is a continuation of U.S. patent application Ser. No. 13/706,201, filed on Dec. 5, 2012, which is a continuation of U.S. patent application Ser. No. 12/594,864, filed Oct. 30, 2009, which is a National Phase Entry under 35 U.S.C. § 371 of PCT App. No. PCT/GB2008/050246, filed Apr. 7, 2008, which claims priority to and the benefit of U.S. patent application Ser. No. 60/922,085, filed Apr. 6, 2007, each of which are incorporated by reference in their entireties.

BACKGROUND OF THE INVENTION

1. Field of the Invention

The present invention relates to a content delivery system of the type that, for example, receives requests for content and sources the request for content from a content source. The present invention also relates to a method of delivering content of the type that, for example, receives requests for content and sources the request for content from a content source.

2. Description of the Related Art

In the field of online knowledge sharing, social networking, collaboration, communication and interactive web sites, two seemingly conflicting trends in the Internet, Search and Telecommunications exist: On the one hand, people are increasingly concerned about privacy and the storage and use of confidential information. Caution encourages people to disclose less information with greater caution and to avoid disclosing potentially sensitive or damaging information. On the other hand, the best search and content retrieval results can be achieved when the search or content retrieval engine has the greatest information about the user. A conflict therefore exists insofar as to get the most out of the Internet, a user must disclose more information, but by disclosing information, the user risks compromising their privacy. It is therefore desirable to maximise relevance and usefulness of search results and content retrieval results without compromising privacy.

It is known for a sensitive, empathetic and articulate human communicator to adopt an appropriate communication style to match the knowledge, frame of reference, character, values and world-view of another party with whom the person is communicating. The communicator makes judgments based on knowledge, emotional intelligence and what is now being called 'spiritual intelligence.' With inappropriate online communication, one may be judged inappropriately with embarrassing results.

Furthermore, a system for online knowledge sharing, social networking, collaboration, communication or an interactive web-site can shape the information provided based on a profile of a user to whom the system is providing information. To the extent that the profile ignores the above character, values, vision, beliefs and world-view of the user, the online system is unable to behave in a manner which is 'sensitive, empathetic and articulate.' Furthermore, a person will reveal different aspects of themselves to different people in different contexts. For example, a profile provided on the LinkedIn professional network may be appropriate for one's professional colleagues, but may be inappropriate for one's family. Similarly, one's profile on FaceBook may be appropriate to friends, but not to professional colleagues.

Web services provide a means for different programs and processes to communicate and thereby construct more complex and functional systems, but the passing of information between web services must be limited by the need for privacy, confidentiality and data protection. Many people avoid risk and limit what they share online, but at the same time give up on the opportunities presented by sharing. As a result, profiles are 'dumbed down' and represent a lowest common denominator without depth or risk. However, the less people reveal of their true character, beliefs and values, the less the opportunity for human connection, empathy and relationship. Internet relationships may therefore tend to be shallow, meaningless and unsatisfying. In this respect, the power of the Internet and web services as a personal and business tool are limited by the lack of depth of personal, private and biometric information available to computer systems and intelligent devices for processing and the need for personal and organisational privacy. Without deep profiling and use of profiling information, the intelligence of intelligent devices is limited. A building or a motor vehicle could behave more appropriately if it could sense that the user was under stress or even cold. Likewise, an online advertising service could provide more appropriate, more profitable advertisements if it knew that the user was a cameraman who liked a particular brand of hardware. A medical products website could target advertising and content delivery more appropriately if it knew that the user was a diabetic. The user is, however, rightly unwilling to make all of their information available to all of these different devices and services.

SUMMARY OF THE INVENTION

According to a first aspect of the invention, there is provided a content delivery system comprising: a trusted holder of profile data arranged to store information concerning a conscious entity; a content delivery requirement entity; a content intermediary entity; and a source of content; wherein the trusted holder of profile data is arranged to issue profile reference data to the content delivery requirement entity in response to a request therefrom, and to communicate the profile reference data and at least part of the stored information concerning the conscious entity to the content intermediary entity, the request for content provision being capable of identifying the conscious entity to the trusted holder of profile data; and the content intermediary entity is arranged to source, when in use, relevant content from the source of content using the at least part of the stored information concerning the conscious entity.

The content intermediary entity may be a software application, a web site, a web service or any other suitable device or entity capable of receiving and using the at least part of the stored information concerning the conscious entity to source the relevant content from the source of content.

The content delivery requirement entity may be any suitable entity capable of requesting provision of content to the conscious entity, for example a web site, web service, agent or other software application which may for example be embedded in a mobile telephone, computer, garment, motor vehicle or building.

The source of content may be any suitable content resource that may be queried, searched or mined for the relevant content, for example a database, such as a media database.

The source of content may be arranged to compile the relevant content in response to the query including at least part of the stored information concerning the conscious entity.

The trusted holder of profile data may be arranged to permit management, maintenance and/or upgrade and to ensure the security of profile data stored, while serving a plurality of devices and/or web sites with appropriate information, where appropriate, anonymously.

The trusted holder of profile data may be a database of elements of information categorised by or which may be queried according to conscious entity type to which each applies as well as the physio-psycho-social state(s) of the conscious entity at which or to which the information element is relevant, for example, the state may be under stress and the relevant information may relate to when a subject is under stress.

The conscious entity may be a person, and may in generality be any system which may be, for example, a person, an organisation, a team, community, social network, town, society, or device, or location, or electronic, electromechanical or physical system.

The content delivery requirement entity may be arranged to receive identity data identifying the conscious entity.

The identity data may be a name and/or a password associated with the conscious entity.

The identity data may be received from a communications device associated with the conscious entity.

A change in the at least part of the stored information concerning the conscious entity may trigger the content delivery requirement entity to request sourcing of the relevant content.

At least part of the stored information concerning the conscious entity may comprise profiling information compiled by measuring habitual thought patterns.

The measurement of habitual thought patterns may be by measurement of brain physiology and recorded for the conscious entity as a plurality of brain physiology types, for example by questionnaire, behavioural analysis or the collection of biometric data.

The at least part of the information concerning the conscious entity may be information concerning a preference of the conscious entity. The at least part of the information concerning the conscious entity may comprise a function. The function may be performed by executable software data. The use of scripts or formulae for deriving the contents of an Access Control Group is a particular case of a general capability where either a profile element or an access control group may contain executable data, scripts or software programs which are stored in the CPD and may be executed by the CPD or by other clients of the Web Service provided by the CPD.

The at least part of the information concerning the conscious entity may comprise an identity, context and/or location and may be any other suitable information relating, regarding or belonging to the conscious entity and/or may comprise a number of profile elements.

The at least part of the information concerning the conscious entity may comprise personal information, for example but not limited to profile, identity, context and/or location information and/or personal content including purpose, vision, values, intensions, observations, definitions, recommendations, intentions, objectives, projects, actions, maturity levels, measures, issues, risks, blogs/blog entries, wikis/wiki entries, documents, media, databases, records and/or fields.

The at least part of the information concerning the conscious entity may comprise personal information collected which may include profile information. The profile information may be collected by a plurality of means and in a plurality of forms. A profile element may result from a test which returns results according to a model for understanding social, psychological and/or physiological state of a conscious entity, for example a questionnaire, sampling, survey, biometric and/or observation. The test may be implemented through a device or software user interface with input through the device. The device may include a means to assess the social, psychological and/or physiological state of a person and/or group of people, for example by means of an electromagnetic, biometric, bioenergetic and/or other suitable device for sensing, for example heart rate, brain wave pattern or other biometric information which sensor may be included as a function of any device.

The at least part of the information concerning the conscious entity may be formed from a profile analysis resulting in one or more profile elements consisting of continuous or discrete rating in one or more dimensions, for example using models of Spiral Dynamics profiling system for people and/or groups and/or an Enneagram personality profiling system. Some of the information collected may be in the form of a profile, for example including a learning style, such as Neurolinguistic Programming (NLP) categories. Examples of NLP categories may include, but are not limited to: visual, auditory and/or kinaesthetic.

The at least part of the information concerning the conscious entity may relate to location of a user, for example, based upon a cell phone cell, Global Navigation Satellite System (GNSS) information received and/or local Bluetooth location information or any other suitable location determination mechanism. The local Bluetooth location information may be obtained from a device of known location communicating with the communications device using the Bluetooth communications interface.

Some of the information collected may relate to linguistic information, for example linguistic information present in the words typed in a software application. Some of the information collected may relate to the proper nouns used within a software program, for example use of a proper noun within a word processed document. Some of the information collected may be in the form of a profile, for example a survey demographic. Some of the information collected may reflect the staged developmental psychology of an individual based on the Spiral Dynamics methodology. Some of the information collected may be in the form of a profile including mindset and values-system as defined in a CTT 7 Levels of Consciousness profile. Some of the information collected may be from internet behaviour and history, for example search topics and sites visited.

A plurality of parts of profile information may be combined into the profile for a single conscious entity. The at least part of the information concerning the conscious entity may relate to an organisation, community or other conscious system or aggregate of conscious entities.

At least part of the stored information concerning the conscious entity may comprise current location information associated with the conscious entity.

The current location information may be derived from use of software programs and/or communications-enabled device, for example a computer or a portable communications device, such as a cell phone.

At least part of the stored information concerning the conscious entity may comprise context information.

The context information may relate to a current activity of the conscious entity. The context information may be derived from use of a software program supported by a computing device. The computing device may be a computer or a portable communications device, such as a cell phone. The computing device may be incorporated or embedded in another structure, for example an automobile or building or garment or any other suitable device, for example an electromechanical device.

The system may further comprise a software application arranged to identify the conscious entity to the content delivery requirement entity. A communications device may be arranged to communicate the identity of the conscious entity from the software application to the content delivery requirement entity.

The content delivery requirement entity may be any suitable entity capable of requesting delivery of content. The delivery of content may be to the software application and/or the communications device.

Content may be delivered via multiple content intermediary entities to a single user or demographic with a combination of multiple media and/or simultaneously, sequential and/or asynchronous delivery to multiple devices. The content may be broadcast synchronously to many users, for example by a multi-cast. The communication to many users may be distributed as one signal and only split and duplicated where the network connection to those users diverges. The information sent to the communications device may consist of a number of segments where the content of each segment may depend on the profile of the user at the particular time. The content of segments may depend on user actions or responses, for example creating a control loop whereby content provided varies in response to a response of the conscious entity. The information provided may be in one or more display areas of the communications device. The information provided in different display areas may be selected depending on user profile and user actions. It may be prescribed that an advertiser using the content delivery system must agree to a code of conduct to use the service. A user may define the profiles of an advertiser that they are prepared to receive advertisements from. A user may prescribe the advertisers from which they prefer to receive advertisements. A user may receive a rebate on amount spent by them recommended by the system or the amount earned by the provider of the system due to their activity.

The content intermediary entity may be arranged to provide reference data relating to the sourced relevant content found.

The content intermediary may be arranged to provide data associated with the sourced relevant content in response to receipt of the profile reference data from the software application. The content intermediary may be arranged to communicate the data associated with the sourced relevant content to the communications device.

The profile reference data may be authority data. The authority data may be a certificate.

The content intermediary entity may be arranged to process requests for data where the recipient of the data to be sourced is anonymous with respect to the content intermediary entity.

The at least part of the stored information concerning the conscious entity may have a legitimate user associated therewith.

The profile reference data may be communicated by the content delivery requirement entity to the software application.

The communications device may be arranged to support a private communication. The private communication may exclude the content delivery requirement entity.

According to a second aspect of the invention, there is provided a content intermediary apparatus comprising: a processing resource capable of receiving profile reference data and at least part of information concerning a conscious entity; and the processing resource is arranged to source, when in use, relevant content from a source of content using the at least part of the information concerning the conscious entity.

According to a third aspect of the invention, there is provided a trusted holder of profile data apparatus comprising: a store for storing information concerning a conscious entity; a processing resource capable of generating reference data in response to request for the reference data; and the processing resource is arranged to communicate, when in use, the reference data and at least part of the information concerning the conscious entity for sourcing of relevant content, communication for sourcing of relevant content being in response to the request for the reference data.

The reference data and the at least part of the information concerning the conscious entity may be communicated to a content intermediary entity.

According to a fourth aspect of the invention, there is provided a method of delivering content, the method comprising: a trusted holder of profile data retaining information concerning a conscious entity; the trusted holder of profile data issuing profile reference data to a content delivery requirement entity in response to a request therefrom, the request for content provision being capable of identifying the conscious entity to the trusted holder of profile data; communicating the profile reference data and at least part of the stored information concerning the conscious entity to a content intermediary entity; and the content intermediary entity sources relevant content from the source of content using the at least part of the stored information concerning the conscious entity.

It is thus possible to provide a content delivery system and a method of content delivery that is capable of providing highly personalised and valuable search and content retrieval results without disclosing more confidential information concerning a subject of the confidential information than permitted by the subject or owner of the confidential information. The resulting system and method is thereby capable of delivering highly personalised content based on private information, without disclosure of the private information.

It is thus also possible to ensure that the owner or legitimate user of the private information can use the private information for search and content retrieval without ever disclosing the identity of the subject to which the confidential information relates. There is therefore no risk associated with receiving information on, for example, a medical condition if only the recipient of the information concerning the medical condition knows who received the private information and the contents thereof.

The power of personal information can therefore be used to a much fuller extent in order to get the best possible value from a global information resource such as the Internet without compromising privacy. Furthermore, physical devices, for example computers, mobile phones, automobiles and buildings can be improved by better responding to the profile of their user or the profile of the system with which they interact.

The ability to provide the right information to the right person at the right time in the above-mentioned manner enhances the value of computer systems and the motivation for investment in computer systems. Similarly, in the context of media, for example television, entertainment, "edutainment", and video communications, the matching of what a viewer or recipient wants and needs with the content of the communication delivered also enhances the value of the media. In this respect, when there is a good match, value is created and the provider of content has the opportunity to derive profit, for example from subscription or advertising, and the user receives positive benefit. Indeed, vendors of next generation high bandwidth internet technologies for video broadcast and transmission, for example Cisco Systems, Inc. can therefore deliver next generation personalised video broadcasting. In this respect, such a service can be sold to corporations for internal and external communications and/or to television stations and/or content owners, for example on a license, lease or revenue share basis with revenues derived for example from subscription or advertising. At best, such communication can be used responsibly to aid the positive development and evolution of the recipient as a human being. Furthermore, media can be delivered so as to further the best interests of recipients, organisations and society as a whole.

It is also possible for vendors of next generation video enabled mobile phone handsets and other portable devices, wishing to profit from increased usage of their devices, to allow consumers to manage their profile including Identity, Context and Location (ICL) and to stimulate users to access greater data volumes of media selected based on this ICL. Similarly, increased value from content can be derived by vendors of bandwidth and the content to mobile phone handset and portable device users.

Additionally, where creators and vendors of "applications real-estate", in particular but not exclusively vendors of packaged software, for example Microsoft Corporation, have large installed bases, but are threatened by free and open source software alternatives it is nevertheless possible to derive advertising revenues from their entire installed base and potentially augment or replace license revenues with advertising revenues. Also, it is possible to create software that interacts more effectively with users by providing a user interface and experience more sensitive to their ICL so as to deliver rich and dynamically constructed media.

Creators and owners of website real estate including makers of corporate intranet and internet portals are able to provide a next level of value based on personalised content and potentially to derive revenues from advertising or merchandising. Furthermore, advertisers wishing to maximise economic value can do so based on on-line spending due to advertising personalised to ICL, for example in respect of principles and values, preferred advertisers, communications style, demographic, medium and content. Also, advertising agencies are able to deliver a new level of value to clients.

In addition, benefit is derived by people, organisations, groups and communities wishing to develop, grow and transform in order, for example, to achieve improvement, performance and success.

BRIEF DESCRIPTION OF THE DRAWINGS

At least one embodiment of the invention will now be described, by way of example only, with reference to the accompanying drawings.

DETAILED DESCRIPTION

Figure 1:
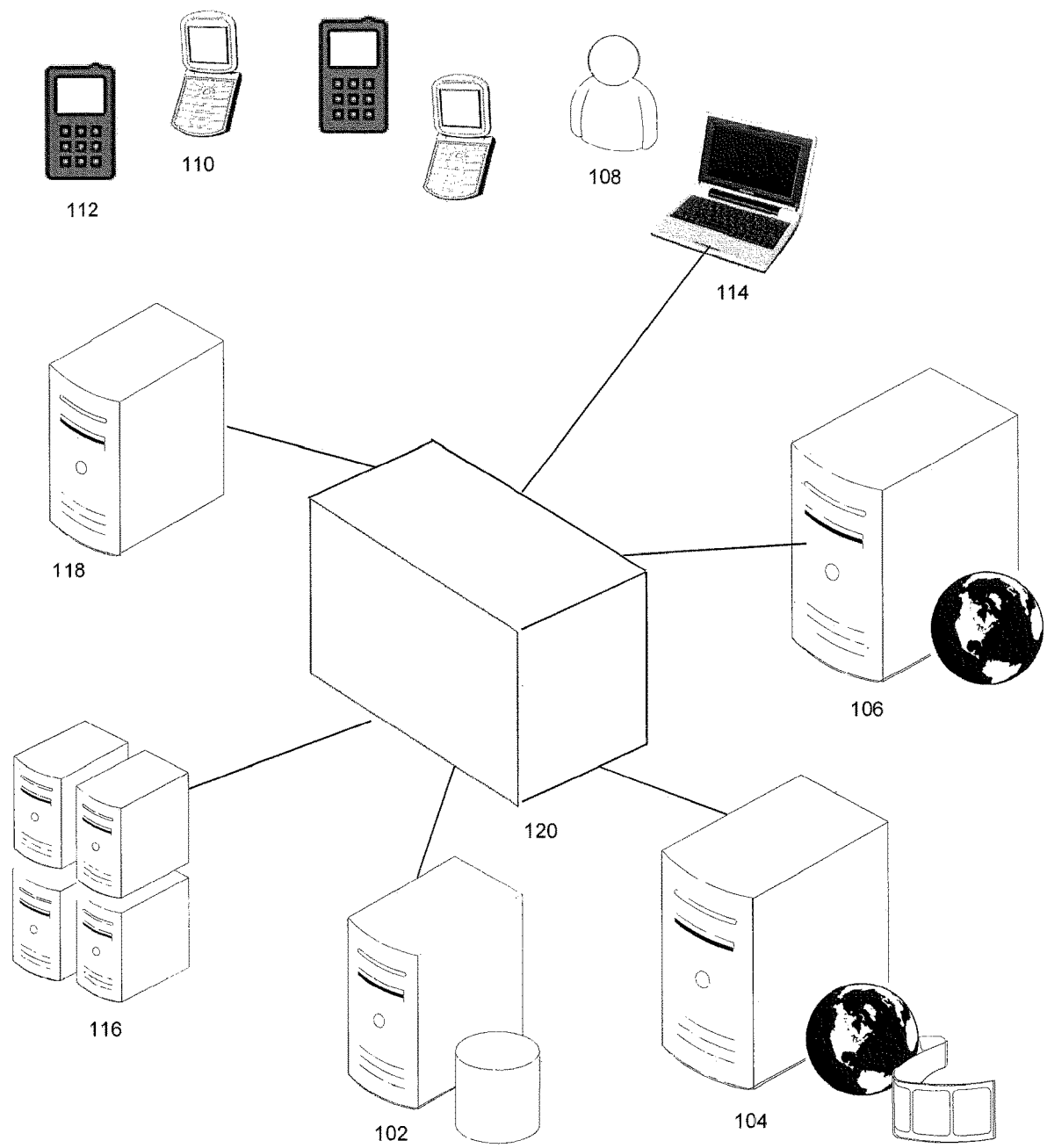
FIG. 1 is a schematic diagram of a content delivery system constituting an embodiment of the invention.

Throughout the following description identical reference numerals will be used to identify like parts.

While the current embodiment is described as implemented, at least in part, using web services communications between servers, programs and devices, in generality, the current invention may be embodied in other systems configurations and using other means of transferring information.

In generality, the embodiments described herein enable a plurality of interconnected server devices and client access devices to interoperate through software, for example web service calls, to provide improved value and privacy in content delivery.

Referring to FIG. 1, a content delivery system 100 comprises a database server 102 to run a Central Profile Database (CPD). A Streaming Media Server 104 and Content Management Server 106 of the system 100 are capable of communicating with each other and the database server 102 via a communications network, for example the internet 120, and delivering media to a user 108 through client devices, for example a cell phone 110, smart phone 112 and laptop 114, or any other suitable device, for example a PDA.

The contents of the CPD database can also be used via a web service by other applications indicated by an Application Server 116 of the system 100.

Figure 2:
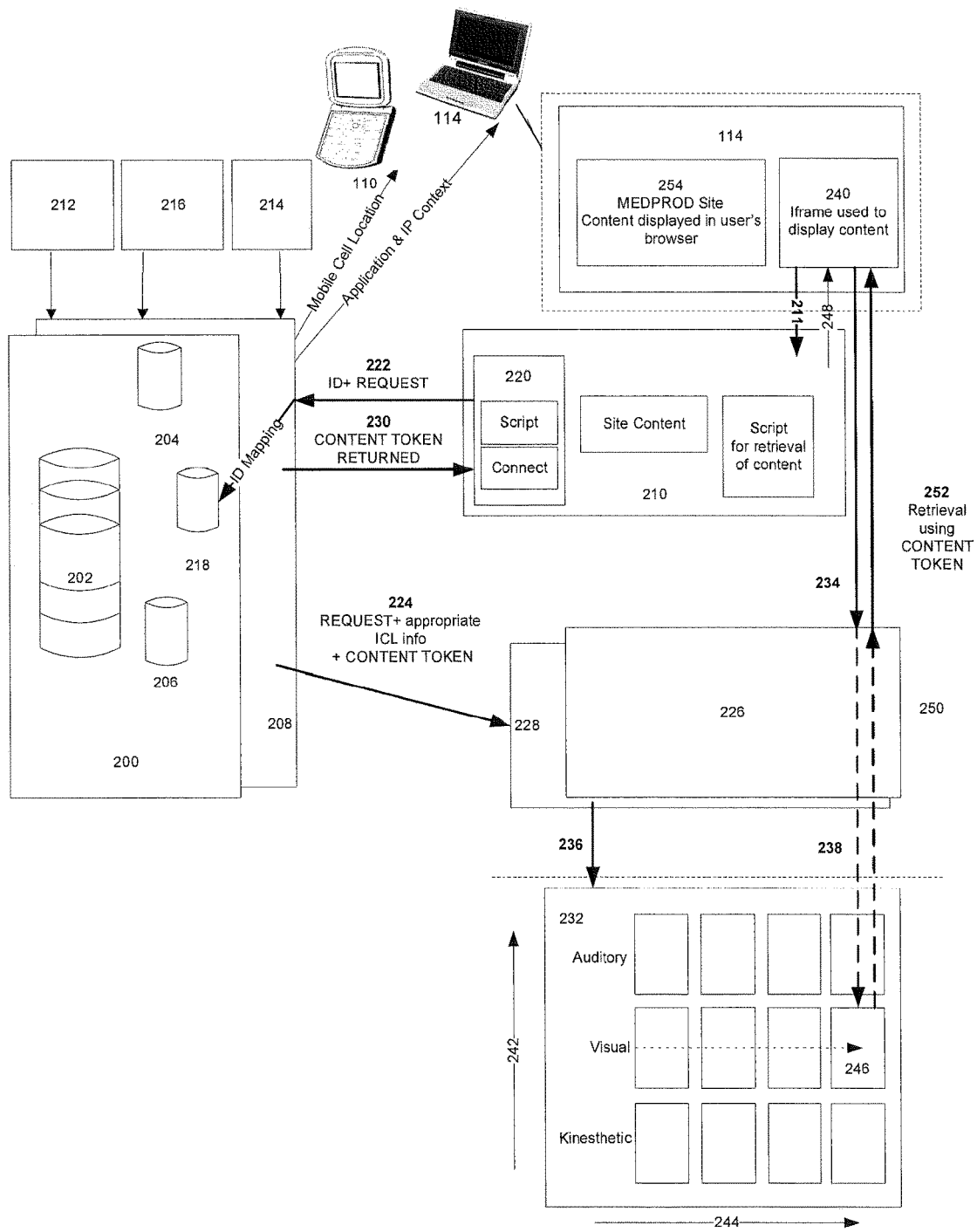
FIG. 2 is a schematic diagram of the content delivery system of FIG. 1 in greater detail.

Turning to FIG. 2, the Central Profile Database (CPD) 200 mentioned above stores a PROFILE table 202 comprising identity profile, context and/or location information for users. The CPD 200 also stores a PARTNER SITE TRUST table 204 and an access control group table 206 together comprising details of which other users or groups can see each aspect of the user's profile. Whilst for the purposes of describing the embodiments herein it is assumed that the skilled person is aware of how to transmit information securely between certified users and servers. CPD 200 has its own certifying authority able to grant security certificates to servers and users enabling them to communicate securely under delegated authority from CPD 200. This ensures that when a web service request is received from a server or user, it can be identified as being from that server or user and hence trusted. The CPD 200 provides a web service 208 which manages personal identity and other information for its users in an integrated, secure and confidential manner.

A Client Web Site (CWS) 210 supported by the Application Server 116 communicates with a number of applications and devices, for example the laptop 114. The CWS 210 is one of a number of CWSs (212, 216, 214) collectively allowing users to edit and change profile information which may be saved back to the CPD 200 by means of the web service 208 initiated from a computer or laptop 114 or web site or from a device, for example the cell phone 110, for example by means of a dedicated web page or web service. In this example another CWS, SOCNET 212, a social network website saves a copy of the user's profile information within its own database. However, a medical information site 214, MEDSITE, does not save confidential medical information other than in the CPD 200. This information is only saved within the CPD 200 which is intended to provide security and confidentiality of personal information.

In this example, a user Peter Simpson edits a profile page in a web browser of the social networking site SOCNET 212 some elements of which are as summarised in Table I below:

TABLE I

| Name: | Peter Simpson | Access Restriction: Public |
|---|---|---|
| Location: | London | Access Restriction: Public |
| Id: | PSimpson | Access Restriction: Logged in users |
| Tel: | +44 207 387 8888 | Access Restriction: Private |
| Learning Style: | Visual | Access Restriction: Friends |

The same user has a further profile in the medical information web site MEDSITE 214 including elements as summarised below in Table II:

TABLE II

| Name: | Peter Simpson | Access Restriction: Logged in users |
|---|---|---|
| Id: | PeteS | Access Restriction: Logged in users |
| Mobile | +44 7710 300 000 | Access Restriction: Private |
| Medical | Diabetic | Restriction: Health Advisors |

In this example, the SOCNET 212 and the MEDSITE 214 save their profile information for Peter Simpson to the CPD 200 by means of a web service 208. Peter Simpson also uses the CPD 200 to improve the quality of information he receives from his employer's, CORP, corporate communications department and generally from a corporate portal, COPORTAL 216.

In this example, the user 108 has participated in a Hewitt Employee Engagement Survey and results of the survey show that he is an "Enthusiastic Follower". However, the skilled person should appreciate that information concerning a user can be processed in any other suitable manner, for example another type of survey for demographic derivation which can then be included in Identity-Context-Location (ICL) data associated with an individual. In this example, the information for Peter Simpson was manually entered. However, the information can be automatically delivered to the CPD 200 and added to the user's profile with his permission. Neither the survey company, nor his employer need to know his personal profile or demographic. In this example, Peter Simpson prefers to keep this information private, as do other of his colleagues, some of whom are less enthusiastic individuals, profiled as "Embittered Detractors", for example. In this example, the user (Peter Simpson) has chosen to allow the CPD 200 to improve the information delivered to COPORTAL 216 by using information from his ICL stored in the PROFILE table 202. Neither CORP, nor COPORTAL has access to Peter Simpson's confidential ICL or to the ICL-based content retrieved during this process. The net result is that Peter Simpson's experience of corporate communications and the value of the corporate portal are improved, based on confidential information, but Peter Simpson's privacy is protected in the process. The user 108 is always in control of his information and can make ICL information available anonymously to improve the information he receives at his discretion.

Table III below sets out exemplary profile information stored for the user in respect of his membership of the corporate portal, COPORTAL, with Peter Simpson's demographic "Enthusiastic" from the Hewitt engagement survey.

TABLE III

| Name: | Peter Simpson | Access Restriction: Logged in users |
|---|---|---|
| Id: | PeterJSimpson | Access Restriction: Logged in users |
| Employer | COCORP | Access Restriction: Private |
| Engagement | Enthusiast | Restriction: Private |

Table IV below is an example of the ICL data that can additionally be stored in the CPD 200 in respect of the user.

TABLE IV

| | Examples | Basis for match |
|---|---|---|
| Name | Peter Simpson | |
| Title | Mr. | |
| Designation | Pete | |
| Birth Name | Peter James Simpson | |
| Address 1, 2, 3, . . . (physical) | | |
| E-mail 1, 2, 3, . . . instant messaging | | |
| Phone 1, 2, 3, . . . | | |
| VOIP 1, 2, 3 | | |
| Website 1, 2, 3, . . . | | |
| DOB | | Same year, same month and day same date |
| Symptoms and medical conditions | | Similar symptoms and medical conditions used to match with other people. Also content related to symptoms and conditions |
| Children | 2 | |
| Significant other | Name, ID | |
| Child 1 | Name, ID | |
| Child 2 | Name, ID | |
| Languages | English, French | English or French content and people who share a common language |
| Psycho demographic profile; mindset, worldview, value system, conscious development | For example Spiral Dynamics vMeme which indicates expected mindset and mental models. In this case, vMeme is Orange, Achievist | |

TABLE IV-continued

| | Examples | Basis for match |
|---|---|---|
| Survey profile 1, eg Life Engagement | Enthusiastic Follower | |
| Cultural background | English/Middle Class Christian | Match with others of like background |
| Principal (family) Religion | Christian | |
| Religious Approach | Liberal | |
| Secondary (lived) Religion | Buddhism | |
| Religious Approach | Liberal | |
| Enneagram Personality Type | 5 (Investigator) with 6 (Loyalist) and 4 (Individualist) wings | Communication appropriate to 1 |
| Ethnicity | Anglo Indian | |
| Learning Style | Visual | Ads/Content presented visually |
| Biometrics | Pulse rate, ECG, EEG, EMG, galvanic skin response, brain signals, respiration rate, body temperature, movement facial movements, facial expressions and blood pressure and other biometric | Content matched to mod and needs |
| Demographic Group (Hewitt Engagement | Enthusiastic Follower | Communications matched to profile of passionate advocate |
| Myers Briggs (MBTI) | INTP (Introvert, Intuitive, Thinking, Perceiving) | |
| Astrology Sign (character) | Aquarius | |
| Astrology North Node (Purpose) | | |
| Astrology Rising Sign (Emotion) | | |
| Numerology Birthdate (Purpose | 7 Researcher | |
| Numerology Destiny | 1 Leader | |
| Professional (1, 2, 3) | | |
| Organization Name, IPI Business Unit | CORP | |
| Title | Producer | |
| Role | Documentary Film Maker | |
| Function | Camera | |
| Security Level | | |
| Preferred Advertiser | Low Price Guarantee, | Advertisers who guarantee to match the best price for the same product |
| Attributes | Free Delivery | |
| Preferred Advertiser Name | Sony, Mercedes, Apple | Advertisers for Sony, Mercedes and Apple |
| Current product | Professional movie | |
| Interest | Camera, sports car | |
| Access control groups | While access control groups may be considered as logically a part of the IPI and ICL, in the embodiment described herein, they are stored physically by use of additional tables. See FIGS. 2 and 3 | |
| Hierarchy of Intent HOI—Purpose, Vision, Life Areas, Intentions, Measures, Actions | | |
| Personal HOI | This is a hierarchy of Life Areas, Life Goals and sub-goals in areas | |
| Career HOI | Career HOI Purpose: Use media to uplift Area: New Projects Intention: Documentary on New Media Action: Buy high-end camera Action: meet Rod Johnson regarding production | Keywords identified from HOI include "Buy" and "Camera" Also "Meet" and "Rod Johnson" |

TABLE IV-continued

| | Examples | Basis for match |
|---|---|---|
| Organization HOI | | |
| Community Memberships | | |
| Demographic membership | | |
| mailing list membership | | |
| other membership | | |
| Access Control (Permissions and Masks) | For each element of the ICL, permissions can be defined allowing appropriate ICL subscribers to access and use the ICL content. Refer to FIG. 2 for the tables that store this information in the current embodiment | |
| Trusted Certificates | ID of others who are fully trusted | A special case of Access Control Group |
| Location | | |
| Location (Applications) | UK/London/Marylebone | Match people in same location |
| Location (OS) | Country + Map References | Proximity |
| Location (mobile cell location and name) | London West End | |
| Bluetooth Location | Pavilions Shopping Centre | Proximity |
| Location (based on IP address) | London Marylebone | |
| Location based on mast serving serving the cell | London Marylebone | |
| Location based on satellite and optionally fixed mast, aircraft, airship, serving cell | | |
| Current Context | | |
| Current activity context | www.thissie.com Cheapflights.com or MS word | |
| Current focus | This may include any information from applications or devices which the user is currently using, accessing, or logged into, see below. | Trigger events, eg., switch application, change device, move focus within application. In background triggered by these events, CPD is updated on my behalf which means that any application or web services I have working for me in background will be able to optimize based on all this information |
| Internet Behaviour | Current search habits, sites, content | Match advents for relevant products, services |
| Preferred Devices | Preferred media for receiving content | Match media delivery with preference |

Location information in respect of the user is derived from the cell location of the user's mobile phone 110 although more detailed location information can be obtained if the user's communications device is equipped with a Global positioning System (GPS) receiver Bluetooth or the like. The information is transferred to the CPD 200 via a Web Service 208. The mobile phone 110 or laptop can also include a biometric sensor which senses one or more of Pulse rate, ECG, EEG EMG, galvanic skin response, brain signals, respiration rate, body temperature, movement facial movements, facial expressions and blood pressure. Furthermore, context information and potentially also IP address and hence location information can be derived from the user's current settings and activity of their laptop computer 114, for example current application in use, and is transferred via the Web Service 208 to the CPD 200.

The user 108, Peter Simpson, is able to positively confirm his online identity with various sites by providing IDs and passwords to CPD 200. In this case for PSimpson is his identity in SOCNET 212 PeteS in MEDSITE 214 and PeterJSimpson in COPORTAL 216. The CPD web service confirms the existence of the three accounts by reference to the appropriate CWS and stores linkage information in an IDENTITY table 218. An example of the IDENTITY table is set out below in Table V:

TABLE V

| ID Auto Increment | CPD Owner CPD ID of owner of identify | APP_SOURCE Application (CWS) to which ID relates | APP_UID This is the identity of the user in the application | APP_PSWD This is the password of the APP_UID in APP_SOURCE |
|---|---|---|---|---|
| 1 | 1 | SOCNET | PSimpson | Encoded password |
| 2 | 1 | MEDSITE | PeteS | Encoded password |

TABLE V-continued

| ID Auto Increment | CPD Owner CPD ID of owner of identify | APP_SOURCE Application (CWS) to which ID relates | APP_UID This is the identity of the user in the application | APP_PSWD This is the password of the APP_UID in APP_SOURCE |
|---|---|---|---|---|
| 3 | 1 | COPORTAL | PeterJSimpson | Encoded password |
| 4 | 2 | SOCNET | RJones | Encoded Password |
| 5 | 3 | SOCKET | LDavies | Encoded password |

The IDENTITY table in Table V above indicates that PSimpson in SOCNET and PeteS in MEDSITE are the same person with the CPD identity 1 in a USER table stored by the CPD 200. An example of the USER table is set out below in Table VI:

TABLE VI

| ID User is referenced with this id later in CPD | CPD_USER_ID Unique user id name | CPD_PASSWORD This is one main, unique password to CPD |
|---|---|---|
| 1 | Peter | Encoded password |
| 2 | Rjones | Encoded password |
| 3 | davies | Encoded password |

Referring to Figure V, the IDENTITY table comprises five mappings, representing three unique CPD IDs. Three of the five IDs are for SOCNET 212, one is for MEDSITE 214 and one is for COPORTAL 216.

The CPD 200 also stores details of values and access settings for profile elements of each user constituting an Individual Personal Identity (IPI) and more generally Identity, Context & Location (ICL) in the PROFILE table 202, an example of which is set out below in Table VII:

TABLE VII

| ID | CPD ID | Access | Identifying | Name | Value | Source Site |
|---|---|---|---|---|---|---|
| 1 | 1 | Public | Identifies | Name | Peter Simpson | SOCNET, MEDSITE |
| 2 | 1 | Public | Anon | Location | London | SOCNET |
| 3 | 1 | Private | Identifies | Tel | +44 207 387 8888 | SOCNET |
| 4 | 1 | Friends | Anon | Learning Style | Visual | SOCNET |
| 5 | 1 | Private | Identifies | Mobile | +44 7710 300 000 | MEDSITE |
| 6 | 1 | MEDSITE Health Advisors | Anon | Medical | Diabetic | MEDSITE |
| 7 | 1 | Colleagues | Anon | Employer | CORP | CORPORTAL |

Each row of the PROFILE table 202 represents a profile element or item defined by its CPD Owner, the item Name and the Source Site from which it came. By referring to the Source Site, it is possible to have different profile items with the same Name which have originated from different sites but have different meanings. The Source Site field can have multiple values allowing for the same Profile items with the same names to be considered as one item used by more than one source site. Profile items with an Identifying value of "Identifies" are not made available in profile requests in which the user is not to be identified or to be identifiable.

A user can edit different elements of their IPI in the PROFILE table 202 through a CWS or by means of a user interface of the CPD 200. In this example, user interface of the CPD 200 is provided by a web browser running on a computer 114 connected via the Internet, but in other examples the interface can be provided via the mobile phone 110 or any other suitable devices and/or interfaces could be used with appropriate permissions to connect through the web service 208.

It should be appreciated that where the owner of a profile in CPD is described herein, that owner may be a person, demographic group, community, group or organisation or another object or system such as building, motor vehicle or city which may have associated with it profile metadata defined in its IPI and where appropriate ICL, hereinafter referred to as IPI for simplicity. The most general applicable definition for a user should be assumed and the user may also be referred to as a Conscious System.

This profile metadata IPI may be referred to as IPI or ICL (which may includes context and location information) with the most general applicable definition assumed. The user can control how much of that IPI is available to 'IPI Subscribers' for example, other people, organisations including their employer(s) as well as applications and web services. An IPI Subscriber can then use the IPI to communicate more effectively with the owner of the IPI. The ICL includes metadata relating to a user's identity, context, activity and location. The profile of the Conscious System may be used with permission by other Conscious Systems to communicate effectively with the Conscious System. The ICL can be used as metadata for information retrieval. Metadata can include, but is not limited to: personal information derived through any means: name, date of birth, health and family information; languages and dialects spoken/read/written and to what level; mindset, worldview, value system, level of conscious development; personal profile which can include for example, questionnaire of survey results, biometric information, questionnaire results, cultural, spiritual, religious, ethnic, demographic group, preferred learning style, enneagram or other personality type, Myers Briggs profile, Astrology (which may be based on date and place of birth), Numerology (which may be based on date of birth and name); advertiser preferences by brand and characteristic, professional information for one or more professional affiliations: for each professional role or affiliation: organisation name, title, role, function, business unit, position in organisation, relationship to others in organisation, security and access control groups within organisation; hierarchy of intent, which can include for example: personal purpose, vision, life areas, intentions, goals, measures, projects, actions, tasks; communities and groups to which the user belongs, for example web communities, demographic communities, mailing lists; permissions in respect of organisations, groups, sites permitted to see some or all of ICL with permissions associated with each element of content acting as an effective "mask" defining which elements can be seen; and trusted people, organisations, groups and/or personal recommendations of person or organisation which can take the form of endorsements or Trust Certificates, where a Trust Certificate allows one user to certify the trustworthiness of another.

Context and location information may or may not be included in the IPI and can be used to provide or derive further context for selection of relevant content or information as a part of the Identity, Context, Location (ICL). ICL is therefore a more general term than IPI, although herein they may be used interchangeably with the broadest appropriate definition. ICL can include, but is not limited to: location, which can be based on application settings, computer operating system settings, IP address of internet connection, GPS location, Bluetooth identity and Bluetooth derived information on location, cellular telephone cell location or identity, aerial or mast serving that cell however suspended whether fixed, mounted on a balloon, aircraft, satellite or other; current activity: attributes or name of web site used, application used, portal used; current focus of attention: document in focus, words within document, in particular proper nouns within focus document, for example the word "London" in a word processed document; values and principles by which a person operates which may be derived by questionnaire of that person, by polling of others, or otherwise derived, for example implied by their community membership, relationships, spending patterns or other information which may be based on online or offline activities.

In relation to current focus of attention mentioned above, this can include the activity, application or website the user is currently carrying out/using, the device they are using it on and the current focus of attention. For example this might include that the user is editing a document in Microsoft Word on a laptop with the word "London" highlighted. In this respect, the user 108 is editing a document entitled "Report.doc" and has highlighted the proper noun "London". The Current Focus can also indicate that the user has recently used their cell phone to send a text and to whom. Generally the context captures dynamic information which indicates the user's current or recent focus of attention. Context and location can be used together with profile to retrieve relevant content. Changes of context, location or other profile elements also constitute useful information which can be used to predict the current interests and needs of the user enabling permitted applications to deliver relevant and timely content to the user.

Hence, it can be see that elements of the Identity in the IPI can be relatively static, for example Birth Name, while other elements of relevant information can be transitory like the current Context, for example website accessed and the current word being typed in a word processing document and current Location defined by, for example mobile phone cell location. The development and use of a comprehensive Identity-Context-Location facilitates more accurate targeting of people to people and people to services and content.

The skilled person should appreciate that certain profile elements are referenced and used and therefore can be changed by either SOCNET 212 or MEDSITE 214. Although several profile elements can be displayed in a single web page in SOCNET 212, MEDSITE 214 or COPORTAL 216, to minimise possible conflicts, certain elements can be locked and generally on saving, only changed profile elements are written back to the CPD 200. In this example, the PROFILE table 202 stores each profile element as a record.) Where, for example, a profile element changed by SOCNET has been modified by MEDSITE since it was read, the user is prompted to confirm changes on a field-by-field basis.

In this example, MEDSITE 214 is a part of a CPD Network which requires that MEDSITE 214 operates by the principles of the CPD 200, for example in respect of not linking between user identity and private content. In this respect, a provider of the CWS, for example, MEDSITE 214, has legal commitments and responsibilities to operate by certain standards, values and principles in order to receive access rights to the CPD 200. Consequently, while MEDSITE has Peter Simpson as a member, MEDSITE 214 does not seek to use or permit to be used the ICL information of Peter Simpson to retrieve or serve information, other than through the secure and anonymous route of the CPD 200.

Since MEDSITE 214 is a member of the CPD Network and adheres to additional privacy requirements, MEDSITE 214 benefits from a greater TRUST LEVEL that the user 108 has granted to CPD Network members. MEDSITE 214 is therefore permitted "secure read access" to the user's profile. The practical implementation of this permission means that the user receives content relevant to his full profile without any compromise to his privacy and without disclosing to MEDSITE information identifying him that or could be used to identify him. The assignment of TRUST LEVELS will be described in greater detail later herein.

As it is desirable to allow the owner or legitimate user of a profile (consisting of, for example, Identity, Context and Location) to have complete control of their confidential ICL information and at the same time to be able to use fully their ICL information in order to access and use the most relevant and useful content available through multiple web sites and devices, a web service architecture is provided in this example that allows communicating input devices, web sites and databases to read and use the ICL information without knowing whose ICL they are using. At the same time, CWS (including, for example, applications and devices) are able to request content based on the ICL, but the CWS never "touches" the content itself. This is achieved by returning a web services request which can then be executed on behalf of the owner or legitimate user of the ICL in order to retrieve information. Only when the owner or legitimate user is securely logged in to the CPD 200 are they able to access and retrieve information.

To enable the owner of the CPD to define how their ICL information can be used and by whom or what, the PARTNER SITE TRUST table 204 stores default permission settings as well as, optionally, permissions in respect of specific sites which are CWS of the CPD 200, for example, SOCNET 212, MEDSITE 214, COPORTAL 216 and MEDPROD 210. An example of the PARTNER SITE TRUST table is set out below in Table VIII:

TABLE VIII

| ID | CPD OWNER | SITE | TRUST LEVEL |
|---|---|---|---|
| 1 | 1 | Default (sites visited by user) | Public |
| 2 | 1 | CPD Default (sites in CPD Network) | Secure Read Access |
| 3 | 1 | SOCNET | Public |
| 4 | 1 | MEDSITE | Secure Read Access |
| 5 | 1 | MEDPROD | Secure Read Access |
| 6 | 1 | COPORTAL | Secure Read Access |

The PARTNER SITE TRUST table 204 defines the level of access or trust permitted to different potential CWS clients of the CPD 200 in respect of a specific user. In this example in Table VIII, the user (Peter Simpson) can edit this information to balance between privacy and the desire to improve the relevance of content provided through web content delivery sites and through advertisements.

By setting the values in the PARTNER SITE TRUST table 204, the user has defined that by default, for general sites that he visits, only information which is "Public" can be shared. A web services approach to implementation means that for popular sites, the mapping between standard fields of the CPD 200 and site fields can be made, so that the user 108 and other users are able to use the CPD 200 to populate and maintain field values in respect of websites or groups of which they are members, but only to the level of disclosure or trust which he has been defined in the PARTNER SITE TRUST table 204 for each site. In this example in Table VIII, as the user has stipulated that for sites which are a part of the "CPD Network", for example MEDSITE 214, default access rights to the CDP 200 is "Secure Read Access" which means that the user's private information including his medical information, as, for example, a diabetic, can be used to retrieve useful information for him. Otherwise, this private information can only be disclosed to users and web services which are members of the group "Medical Advisors".

It should be noted that the CPD 200 has certain predefined security access groups, for example Public (Web Users); Logged-in Users (users currently logged in), and Private (no user access).

In addition, and as suggested above, pre-named Trust levels are used in the PARTNER SITE TRUST table 204. The "Secure Read Access" trust level mentioned above is used to explicitly define CWS applications and devices which have permission to make requests of the CPD 200 to provide content back to the user, rather than back to the application. By way of further example, a pre-named Access Control Group is "Full Read Access". Members of this group have reader access to all information in the ICL except passwords.

Furthermore, users can add their own Access Control Groups. Definitions for user defined Access Control Groups are stored in the ACCESS CONTROL GROUP table 206, an example of which is set out below in Table IX:

TABLE IX

| ID | CPD OWNER | AGG_NAME | ACG_TYPE | ACG_DEFINITION | SOURCE |
|---|---|---|---|---|---|
| 1 | 1 | Friends | NORMAL | | CPD |
| 2 | 1 | London Friends | COMPOUND | Friends AND Profile.location - London | |
| 3 | 1 | MEDSITE.Health Advisors | REFERENCED | | MEDSITE |

In the ACCESS CONTROL GROUP table 206, the field SOURCE defines the Client Web Site from which the definition is derived where applicable. Each Access Control Group has a type, defined by field ACG_TYPE. By way of example, Access Control Group definitions can consist of user defined lists (NORMAL), referenced access control groups (REFERENCED) and logically defined access control groups (COMPOUND).

Definitions of the Access Control Groups are stored in an ACCESS CONTROL GROUP RELATIONS table (not shown in FIG. 2) and define which users (CPD_USER_ID column) are in which group (ACG_ID column) belonging to the user (CPD Owner column). By way of example, Table X below sets out exemplary entries for the ACCESS CONTROL GROUP RELATIONS table in respect of the Friends group of Table IX:

TABLE X

| ID | CPD OWNER This is the owner of this relation (ID value in USER Table) | ACG_ID This field relates to ID field in ACCESS CONTROL GROUP table (in this case 1 - friends ACG) | CPD_USER_ID This user is a member of the group (ID value in USER table) |
|---|---|---|---|
| 1 | 1 | 1 | 23 |
| 2 | 1 | 1 | 3 |
| 3 | 1 | 1 | 5 |

The user of CPD 200 can define custom Access Control Groups, for example: Friends, Medical Advisors, Trusted Sites, and/or Trusted People. A COMPOUND Access Control Group is defined by a filter or a logical combination of a filter and an existing Access Control Group, for example: (Member of Friends) (Boolean AND) (Location=London), which can be denoted as: Friends AND (Location=London). Another example is: Medical Advisors AND Friends.

Access Control Groups can be defined through a web interface to the CPD 200 or defined in a CWS along with profile information and delivered to the CPD 200 through the web service 208. In this way, the CPD 200 can act as a library of executable scripts defined and shared by clients of the Web Service 208 that the CPD 200 provides. These scripts can require the user to be logged into the CPD 200 or to a partner site or device (CWS) in order to execute and return a result. An application (CWS) can specify an operation which makes use of the confidential information available in the CPD 200, but the confidential information is not 'seen' by the CWS when it is delivered to the user's web browser or other device or application directly.

Figure 3:
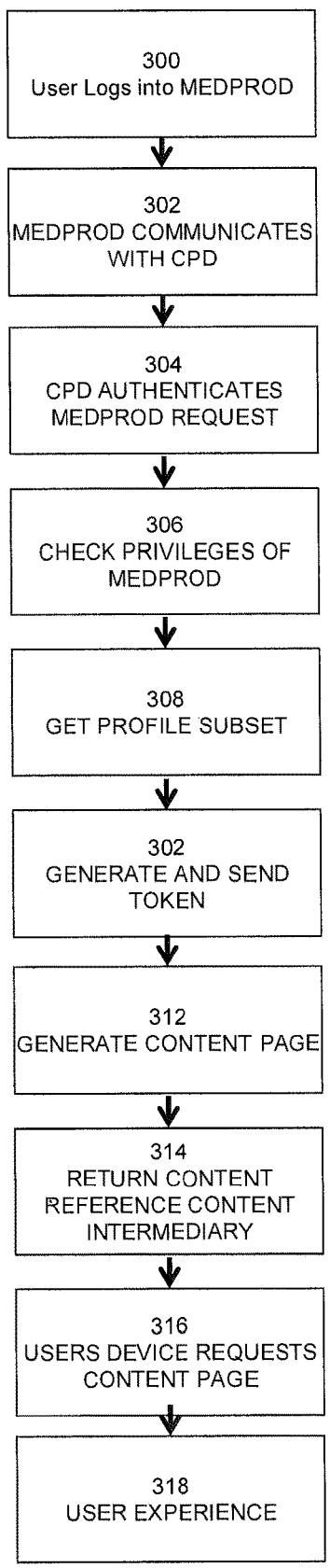
FIG. 3 is a flow diagram of a method of content delivery for the content delivery system of FIG. 2.

In operation, MEDPROD 210 makes a Request 222 and requests Identity, Context and Location (ICL) information from the CPD 200 using a CPD plug-in 220, based on the User ID of the user for MEDPROD 210, a Medical Products Catalogue. (FIG. 3, Steps 300 and 302)

After the user ID and request is sent 222 using the Web Service 208 to the CPD 200, the CPD 200 authenticates the user using the IDENTITY table 218. If this process is successful, the CPD 200 checks for relevant Access Control Groups in the ACCESS CONTROL GROUP table 206 and the PARTNER SITE TRUST table 204 for this request. Based on that information CPD 200 knows which subset of profile data can be used to build content for this request. (FIG. 3, Step 304, 306 and 308)

The CPD 200 then creates a unique random token value with a minimum of 128 bits (the Content Token) which is sent 224 along with a chosen subset of ICL data to Content Intermediary 226 using another Web Service 228. At the same time, this Content Token is also returned 230 to the CPD plugin 220. (FIG. 3 Step 310)

The ICL data sent by the CPD 200 to the Content Intermediary 226 is filtered dependent on the Access Permissions granted by the user of the CPD 200 explicitly or implicitly to MEDPROD 210. For example, since MEDPROD 210 does not, in this example, have Access Permissions of "Medical Advisor", the value of the ICL passed to the Content Intermediary 226 should not include the medical condition of the CPD user (Peter Simpson). However, since MEDPROD 210 is within the CPD Network which has "Secure Read Access", the value of the profile element Medical as "Diabetes" is returned to the Content Intermediary 226 along with other public information and logged in user information.

It is the responsibility of the Content Intermediary 226 to communicate with the CPD 200 and one or more Content Databases, for example Content Database 232. The Content Intermediary 226 ensures that Requests and Content Tokens received 224 are matched with those received 234 from the user device 114, detail of which will be described later herein. Additionally, content requests 236 are made to the Content Database 232 to return appropriate content from the Content Database 222 via anonymous request 238 (FIG. 3, Step 314) to be delivered to an frame 240. The result is that the Iframe 240 provided by the User Device 114 receives content based on the ICL information available according to the retrieval capabilities of Content Database 232 without the user's confidential ICL information being disclosed other than to the CPD 200 and Content Intermediary 226.

In this example, the role of CPD 200 includes a certifying authority and a secure and selective profile database for storing ICL information. The Content Intermediary 226 is capable of communicating with the computing device 114, and serves as an intermediary between content databases and users each certified under delegated authority of CPD to provide the best information to the user, based on the capabilities of the content database given the information available from the CPD 200 while keeping content secure and ensuring anonymity for the user.

Once Content Intermediary 226 receives ICL information along with generated Content Token from CPD 200, The Content Intermediary 226 communicates with the Content Database 232 via the web service content request 236 to generate content based on the request 222 and ICL information received from the CPD 200. (FIG. 3, Step 312) It is important to note that the Content Intermediary 226 has knowledge of the identity of the user and of the ICL. On the other hand, the Content Database 232 has no knowledge of the identity of the user, only of the ICL, whereas MEDPROD 210 has knowledge of the user's name but no information on their ICL content. In this case, the Content Intermediary 226 retrieves from the Content Database 232 content combining medical patient experiences, general information and sponsored links and content. The Content Intermediary 226 uses its authentication with the Content Database 232 to request and receive this information from the Content Database 232. (FIG. 3, Step 314) The Content Intermediary 226 then provides the information to the user device 114 based on the certificate of the user registered with the CPD 200 as certifying authority. In this example, the Content Database 232 provides content to the Content Intermediary 226 which then delivers the content to the user certified with CPD 200 under CPD's certifying authority.

In this example, the Content Intermediary 226 passes through the information to the user without disclosing to the Content Database 232 the identity of the user. In a simple implementation where relatively small amounts of data are involved, for example short video clips, this is achieved by caching the information provided by the Content Server 232 and making it available for retrieval by request 234 retrieved with 252. In this example the Content Intermediary 226 receives content from Content Database 232 and routes it to the appropriate user while protecting the identity of the user from the Content Database 232. An example of this function is by means of retrieving content 246 from the Content Database 232, caching in the Content Intermediary 226 and serving the content to the Iframe 240.

In another example, the content 246 is routed from Content Database 232 to user Iframe 240 more directly as follows. The content to be delivered 246 consists of sequential packets or datagrams of information consisting of address and content. An Internet router receives such a packet and routes the packet appropriately. In this example, the packets are addressed to the Content Intermediary 226 with an indication in the address to which CONTENT TOKEN they relate using any suitable technique known in the art, for example a payload of a packet or a mechanism using another part of the packet for communicating non-protocol data without impairing propagation of the packet from a source address to a destination address thereof. The Content Intermediary 226 receives the packets and replaces the address with the address of the appropriate user. The Content Intermediary 226 does this by matching the CONTENT TOKEN used to construct the request 236 and the CONTENT TOKEN received from the Iframe 240 via the request 234. When receiving content 246, the Content Intermediary 226 receives the content 246 from the Content Database 232 as packets which can be represented, at a high level, as: PACKET=HEADER (ADDRESSES)+PAYLOAD (CONTENT), where one of the ADDRESSES is the destination address of the packet and CONTENT is a portion of the content to be delivered. In this example, the Content Intermediary 226 uses the CONTENT TOKEN, tk, and other parameters to return a value, or content, 246 from the Content Database or Server 232, which value is indicated as CDB(tk) herein. One of the packets returned by the Content Database 232 via return 250 can be represented as: PACKET from Content Database=HEADER(CSadr,tk)+CDB(tk), where CSadr is the address of the Content Intermediary 226. If UAdr(tk) is the address of the user to which tk relates, the Content Intermediary 226 "re-routes" the packet received from the Content Database 232 by modifying it as follows: PACKET from Content Intermediary=HEADER(UAdr(tk))+CDB(tk). In this example, UAdr(tk) represents the recipient address as the Iframe 240. The packet bearing the portion of the content is then received by the Iframe 240.

In this example, the ICL contains information on Learning Style and other Demographic information which is used to select from a (multidimensional) Content Database 232 of, in this example, patient experiences and personal stories, general information, useful non-profit links and commercially sponsored links. In this example, the Content Database 232 comprises an array of possible content selected based on Learning Style 242 and Demographic 244. The appropriate content is identified based on the ICL to be the content to be returned 246.

Although in this example, the Content Database 232 is a simple array, the skilled person should appreciate that more complex techniques can be employed by the Content Database 232 to combine content to create content to be returned 246. For example, the Demographic 244 can be a many-dimensional value as indicated by the simple example of the user 108, Peter Simpson, where Learning Style, Location, and Medical (condition) are elements of the Profile which can be used. Consequently, in this example, the Demographic 244 includes the Medical profile element value "Diabetes" and the location profile element value "London". The Content Intermediary 226 thus provides parameters to the Content Database 232 based on which the Content Database 232 selects content 246 which is relevant to a person with Diabetes in London. (FIG. 3, Step 312) The resulting information is then provided to the user via the user device 114 using the user's authenticated relationship with the Content Intermediary 226. Each of the Content Intermediary 226 and the user of the User Device 114 have a certificate issued under the delegated authority of the CPD 200. Effectively, the Content Intermediary 226 is using its trusted relationship with the CPD 200 to receive the ICL and other information. The Content Intermediary 226 is using its trusted relationship with the Content Database 232 to request and receive appropriate content and using its trusted relationship with the user 108 to return the content 246 while protecting the identity of the user 108 from the Content Database 232.

The Content Database 232 employs an algorithm that weighs different content elements of the ICL to make the best selection of content 246 for the user 108 based on the information request and the available knowledge of the Identity, Content and Location of the user 108. In general, the returned content 246 can be of varying degrees of complexity, for example a simple text string, or a multi-frame web page with multiple simultaneous multimedia streams which are dynamically constructed to best match the ICL of the user 108 of the medical products site MEDPROD 210. Other forms of the returned content 246 include: a web service return value, a web page link, an information package, email, XML data and/or a text message. However, in this example, the returned content 246 is a web content page, the content page being available for a limited period of time following generation thereof and can only be accessed by the correctly authenticated user using a Web Services call with the correct Content Token value to the Content Intermediary 226.

In this respect, the CPD plug-in 220 transmits the Content Token value received from the response 230 via 248 to the Iframe 240 of the User Device 114. The browser running on User Device 114 then dynamically updates a part or whole of the display of the User Device 114 by making the Request 234 to the Content Intermediary 226 with the Content Token. Content Intermediary 226 then makes the Anonymous Request 238 to the Content Database 232. In this embodiment, the retrieval of content into the Iframe has been implemented by dynamically changing the Source parameter of an IFRAME HTML element. (FIG. 3, Step 316)

The selected content 246 is not passed back to MEDPROD 210. Instead, it is returned directly from the Content Database 232 through the Content Intermediary 226 via an Anonymous Retrieval 250 and Retrieval 252 to the browser running on the User Device 114 of the user 108. The selected content 246 can only be retrieved when the browser or device session has an active secure connection to this Content Intermediary 226 and the correct user is authenticated and the correct Content Token is supplied and for the limited period of time in which the content is available. Alongside this content, the user can also view MEDPROD Served Content 254 retrieved from the MEDPROD Web Site 210. MEDPROD has no knowledge of the content of the IFRAME. The Content Database 232 has no knowledge of the user's identity and hence Anonymous Retrieval 250 is shown as an arrow with a broken line as a shaft, to show that the Content Database 232 has no knowledge of the identity of the CPD certified user of User Device 114. The Content Intermediary 226 plays the role of trusted intermediary, retrieving useful information based on private ICL information, without disclosing whose ICL information is being used.

In this example, the user 108, carrying the cell phone 110, is located in "Marylebone", an area in central London. The location can be determined from the cell identifier associated with a current location of the cell phone 110. Context is derived from the fact that the user 108 is currently accessing a medical products database. This information is passed to the CPD 200 implicitly when the MEDPROD database makes its request. As described above, the content returned 246 is dynamically constructed by the Content Database 232 to deliver meaningful and targeted content for the user 108. In this example, this is content about health for diabetics with specific links to commercial organisations and support networks in the Marylebone area of London. The content 246 has been dynamically constructed for the owner of the ICL without any knowledge by the Content Database 232 of the identity of the owner of the ICL. The user 108 is receiving highly appropriate content, based on personal, private and confidential information including links to products on the site MEDPROD 210, without the web site MEDPROD 210 which he is using knowing anything about him, other than his user name and profile as disclosed to the site MEDSITE 214.

In order to construct the Profile for the user 108, profile elements are, in this example, gathered from a plurality sources and devices in the broadest definition, for example databases, mobile devices, online behaviour, search queries made, user interface input, bio-sensors, surveys and questionnaires. MEDPROD 210 then retrieves content from a plurality of content intermediaries certified by the CPD 200, each similar in function to the Content Intermediary 226 and which each can have trusted relationships with a plurality of Content Databases and deliver back content appropriate to the user's ICL to a plurality of devices and interfaces, for example via cell phone text message, web page Iframe or other device which has the equivalent authentication to MEDPROD 210 or other certified entity and the appropriate web service or other suitable interface.

In another embodiment, the delivery of content to the user 108 can be instigated by an independent event, for example by a user action or delivery can be triggered by a change in the ICL, a change in location of the user 108 based on cell phone cell or Bluetooth location information received from, for example a sensor in a local shopping mall. The result is that the user can choose to receive highly tailored information and advertising based on their specific interests wherever they go. For example, advertisements appropriate to current purchasing interests or a current biometric condition.

In the following examples, a similar approach can be used to the embodiment described above in order to achieve dynamic, personalised TV programming, mass corporate communications, improved relevance in a corporate portal and personalised advertising. To implement each of these examples, the Content Database 232, Client Web Site 210 can be replaced by appropriate web service enabled applications to deliver the intended functionality and benefits. The information owner or legitimate user of the CPD 200 may control how their ICL information is used through the trusted relationship with the CPD 200 and a Content Intermediary by a subscribing Client Web Site, for example a TV/Video programming Content Database or an Advertising Content Database, without revealing the ICL information of the user to the subscribing CWS 210.

In relation to advertising, an advertisement is valuable to the consumer when it provides information about a product or service that they would want to know about. The better the match, the more value to the consumer and the more valuable the advertising opportunity to the advertiser. An on-line advertiser most values a click-through from a customer who wants and needs the product or service advertised. The on-line advertiser that can deliver better qualified consumer 'clicks' has potential to capture valuable customers.

Indeed, degree of matching to some or all of profile elements within the ICL can be used in many instances, including but not limited to advertising alone, to recommend connections to people and relevant content, as well as dynamically constructing content and linkages based on the ICL information available for example: Advertisements, People, Organisations, Groups, Communities, Places, Objects, Documents, Video/media content, Products, Services, Web sites, web pages and other content.

Selection of Matching Content can be based on degree of matching between the ICL and the content. Tuning is based on setting the level of influence of each profile element. Different known algorithms can be used for this purpose.

Further examples of applications of the above embodiments include delivery of a personalised CEO message to employees with each employee receiving a personalised message based on what they have revealed of their ICL to a program delivery system. In relation to television programming, personalised television programming and associated advertising is achieved by delivering personalised content based on what the user has revealed of their ICL to the program delivery system. By defining their programming preferences, a user can define their requirements for a personal television channel which television programming suppliers can subscribe to as a part of the ICL in order to deliver content desirable to and relevant to the owner of the ICL. By profiling content for its compatibility to a demographic or more generally to elements of the ICL of users, an individual or organisation can define a television channel which itself can be syndicated and monetised.

In relation to on-line services, an intranet or Internet portal provides personalised content, advertising, applications and/or search results. By using metadata for the user and the metadata for the current context and location as well as user input, for example keyboard, mouse, voice and/or video, a system can be used to automatically deliver search results, or deliver search results on request.

In relation to software applications, for example office applications, such as Microsoft Office, by providing advertising based on the ICL information of users of the software applications, use of the software applications can be paid for by advertising and the supplier of the application can derive revenues on a pay per click or other advertising basis.

In all of the above cases, the advertiser can choose the demographic of target clients by defining a filter on the ICL of target clients to which it wishes to advertise. The advertising server then provides appropriate advertisements, based on the users ICL and preferences and the advertisers preferences. In addition, the advertiser can customise the advertisement served based on the content of the ICL.

Users can set their requirements for acceptable advertising, for example by defining or choosing the values and principles to which advertisements must adhere and declining to receive advertisements or content which is of a violent nature, or advertisements that are animated rather than static or textual for example.

Some of the above examples will now be described in more detail below in the context of the content delivery system 100.

Referring to FIG. 2, the retrieved content 246 includes sponsored links to products in the medical product catalogue of MEDPROD 210. The ICL information for the user 108, for example Peter Simpson, sent by the CPD 200 to the Content Intermediary 226 via its web service 228 includes preferred advertisers and the values and ethics that the user 108 expects of advertisers. This application can be clearly understood by treating the Content Database 232 as an Advertising Content Database. In this example, web services are used to provide useful advertisements to consumers, like the user 108 and valuable potential customer leads for advertisers while keeping the private information and the identity of consumers confidential.

Referring to Table IV above, matching advertisements for the user 108 might be for professional movie camera sales outlets in the West End of London. The advertisements selected can be visually presented for the Learning Style 242 of the user 108 and appropriate to the mindset of achievement of the user 108 and his advertiser selection keywords "Low price guarantee" and his advertiser preference for a particular brand, for example Sony, as an advertiser stored in the PROFILE Table 202 of the CPD 200. The preference for the Sony brand has been derived from the online behaviour of the user 108 as has his preference for "Low price guarantee". His current interest in professional movie cameras was manually entered by the user 108 so that the advertisements he sees will be relevant to what he is interested in. A biometric sensor in his cell phone indicates that Peter has a comparatively low heart rate and is therefore not rushing. It also indicates, based on biometrics whether he responds positively to an advertising message received on his cell phone. This information is always confidential to Peter and only provided securely and anonymously to the Content Database 232 with the anonymity provided by the Content Intermediary 226. Advertisers can create a Content Database 232 of advertising media appropriate to a user's physical, emotional and mental state using biometrics and based on different demographics 244 and/or advertisement media fragments with conditional logic used to construct the advertisement based on the full available ICL of the viewer of the advertisement. Such Content Databases must have the correct authentication with the Content Intermediary 226 and interact with its web service interface 228.

In Table IV of possible ICL content, the user 108 receives a personalised advertisement while in Marylebone, London. This advertising comes via cell phone text message or multimedia message and simultaneously or shortly after based on Peter's positive biometric response, from electronic advertising boards in Pavilions Shopping Centre. By way of example, the advertisement headline presented to the user can read: "See the latest high performance Sony video cameras 5 minutes away—lowest price guaranteed".

The movie camera is offered as it matches the Current Product Interest of the user 108. The advertisement is in the English language to match the preferred language stated in the PROFILE table. The word "See" appeals to the visual learning style of the user 108. The words "High performance" appeal to the achievist psycho demographic of the user 108. The words "Lowest price guaranteed" are based on the Preferred Advertiser Attributes specified by the user 108. Furthermore, the Sony brand is highlighted as it matches the Preferred Advertiser Names field of the PROFILE table. The words "five minutes away" are based on the distance from the location of the cell phone 110 of the user 108 to the retail outlet of the advertiser. The advertisement can include or offer to text message or instant message dynamically generated directions based on the exact location of the user 108 and the retail outlet. Additionally, the advertisement can be a multimedia message with an image of a camera with the words "Get there faster" and "Just round the corner". The visual display appeals to the "visual learning style" known to be preferred by the user 108 and the words "Get there faster" again appeal to the achievist psycho demographic of the user 108. Meanwhile, a video clip advertising the camera can additionally or alternatively be displayed on a nearby electronic bill board.

Hence, it can be seen that the above example combines information from multiple sources including location, internet usage habits, advertiser preferences, personality and biometrics. In addition, the algorithm employed by the Content Intermediary 226 and Advertising Content Database 232 can match the location of a friend or colleague of the user 108 (Rod Johnson in this example) who is nearby and point out his location and provide means of contact, for example instant messaging, Voice Over Internet Protocol (VOIP) phone and telephone numbers.

In the context of personalised mass communications, a video-streamed corporate message from a CEO of an employer, CORP, of the user 108 tailored to each recipient is an example of personalised television programming. The message from the CEO is only valuable when it delivers the right message to the right employee. In addition to employee survey results, a Hewitt Employee Engagement Survey conducted for the employer shows that there are different employee attitude groups, or demographics in the corporation. A different message is therefore appropriate to the different demographics, which in this example are "Passionate Advocates", "Enthusiastic Followers", "Under-Rewarded Supporters", "Disgruntled Coasters" and "Embittered Detractors". The challenge to the provider of the television programming, in this example of Corporate Communications programming, is that the profile and demographics of each employee are private and confidential, yet without accessing them, communications will be less effective. Referring to FIG. 2, the independently managed, personal and confidential ICL of each consenting corporate employee can be accessed anonymously in order to make communications content delivered to each employee most appropriate.

The role of the CPD 200 is to be a trusted third party to enhance the communications between employer and employee without loss of employee privacy. With appropriate permissions, the Content Intermediary 226 and the Content Database 232 are used for delivery of video and other communications content which is tailored to the employees needs. This application can be clearly understood by treating the Content Database 232 as a Corporate Communications Content Database. It can thus be seen that effective corporate communications to each employee can be provided based on, for example, learning style and demographics.

In one example, the corporate message can be delivered to many users in an audio-visual manner as a "video cast" by means known as unicast, broadcast or multicast. The new generation of technology known as multicast allows video signals to be broadcast to thousands of users without duplication of signal between the source and any point. Only when two subscribers are at different IP addresses that must be reached via a different network route does the signal duplicate.

Video and multimedia are increasingly recognised as a powerful communications tool—not just for entertainment, but also for personal development and business transformation. Additionally, corporations want to communicate appropriately to employees and partners. Video casting may be optimised for efficient delivery, but different communities may need different messages. Video casting together with personalising the video content to the needs and profiles of different demographic groups and individuals creates a communications technology of unprecedented power and delivery efficiency.

In this respect, the speech of the CEO mentioned above, or other media broadcast, can start with a general introduction, followed by a communications segment (or multiple communications segments) tailored to the profile of the recipient. Referring to FIG. 2, the following provides an abstract description of how the Content Intermediary 226 and Content database 232 can use the ICL information of a user to deliver personalised video or television programming, including corporate communications.

The structure of the video communication can be described as: VideoCommunication=Segment 1; Segment 2; Segment 3; . . . .

Furthermore, the ICL of a user, u, at time, t, and in location, I, is denoted as: ICL(utl). The Segments mentioned above can be 'programmed' based on the profile of the particular recipient. In this respect, Segment 1 can be general and the same for every recipient. Then, Segment 2 for user, u, at time, t, and location, I, can be determined by a function f2 operating on the profile ICL(utl) and a database of video content Vdb, for example the Content Database 232:

$$\text{Segment } 2 = f2(\text{ICL}(utl), Vdb))$$

$$\text{Segment } 3 = f3(\text{ICL}(utl), Vdb))$$

This streamed personalised video programming can be on-demand or simultaneous videocast to multiple users with dynamic selection of segments to match ICL of each user. This may use video cast IP technologies to only deliver one signal for multiple users subscribed simultaneously to the same fragment as described above. Alternatively, the video programming can be Asynchronous and constructed as above, but when required and/or on-demand by user. Furthermore, the video programming can be Spatially constructed, like a web portal or software application, and within a display of a device multiple frames and/or regions can be presented that may change in structure and individually in content over time. The communications stream delivered to the user may be dynamically selected segment-by-segment based on changes to the ICL, for example, responding to the biometrics of excessive stress appropriately. Also, at least part of the video programming can be delivered across devices, for example versions or elements of the same advertisement can be delivered synchronously, sequentially or asynchronously via computer, television, cell phone, video, telephone and/or other devices.

Furthermore, this same approach of dynamically constructing content applies to web sites, advertising, corporate portals, video and television programming. The stream of media segments created can be programmatically chosen from a library, using the available ICL information, together with user input as parameters to select and sequence media segments.

It should be appreciated that context information can play a varying role in selective content delivery. In this respect, context can be influenced by user input to an application, or by navigation, for example using the mouse, keyboard, Tab key or other key or device to move around content of an application or web page and thereby change context. For example, the Tab key of a keyboard or a mouse can be used by the user to navigate around context, the advertisements of a corporate portal and retrieved content changes accordingly, for example the business results for London retrieved as the user tabs to a page on London. In an application, for example a word processor or spreadsheet, the user may "tab" around Nouns or Proper Nouns within the document as a result of which the retrieved content changes accordingly, for example information on London hotels retrieved as the user tabs to the name London. This retrieval of content may be performed in various ways. For example, the retrieval can be automatic, like predictive or "type ahead", always finding what the user might want to know (if enabled). Alternatively, the retrieval can be user requested in which case the user can activate a search or retrieval of content based on the current available ICL information. In an attentive mode, the user can tab or navigate around ICL information in a contextual search-like manner and retrieve content automatically. Additionally or alternatively, users can choose to select in/out ICL information, as a default or on a temporary basis, for example "Ignore my Hierarchy of intent", "Ignore my personal information" or "Focus on my professional role."

In substantially the same way that Advertising Content can be personalised, so too can video content, making possible dynamically personalised television programming for any combination of information, entertainment and advertising.

Similarly, the video casting mentioned above can be used to reduce loss of viewers by television channels to on-line alternatives and so reduce loss of advertising revenues. The upcoming generation expects a more interactive and personalised experience. Broadcasting multiple content streams, together with personalisation of the video content to the needs of different demographic groups and profiled individuals within those groups in the above-described manner, creates the potential for a new generation of personalised television.

In the context of a corporate portal or on-line portal, such portals are most valuable when they delivers the right information, delivered in the right way to the individual user, user demographic or organisation.

Returning to the example of the corporate portal, COR-PORTAL 216, the independently managed, personal and confidential ICL of each corporate employee can be accessed in order to make communications content delivered to each employee most appropriate. This application can be clearly understood by treating the Content Database 232 as a Corporate Portal Content Database. Hence, effective corporate communications can be provided to each employee based on, for example, learning style and demographics. In this example, the demographics of the Hewitt Survey ensure that corporate communications are appropriate while keeping the private information and the identity of employees confidential.

In another example, desktop applications and corporate portals can have more personal and demographic information which is not used for advertising. By leveraging the demographic information in desktop applications and portals, providers of these applications have the potential to derive significant revenues from advertising. In this respect, a Desktop Application is connected by a plug-in, similar in function to the CDP plug-in 220 mentioned above, and an Iframe similar in function to the Iframe 240 mentioned above, to support the same Web Services communications 222, 230, 234 and 252 and so to provide personalised content based on the ICL within desktop applications for example as an advertisement. For example, a user of Microsoft Word types London and sees adverts related to London that are presented in an appropriate way to their learning style and personality.

Mobile devices, mobile phones and personal music players, for example, are increasingly used as capture and display devices for a growing global library of content. By enabling a user to get exactly the content to meet their needs, vendors of content, embedded advertising, airtime and bandwidth can increase revenues from this important new delivery channel. Referring to FIG. 3 again, a mobile device software application may be connected by a software module, similar in function to the CDP plug-in 220 mentioned above, and a user interface element similar in function to the Iframe 240 mentioned above to support the same Web Services communications 222, 230, 234 and 252 and so to provide personalised content based on ICL within, for example, a web browser or a software application running on the mobile device.

Video database content selected based on the ICL and delivered via IP network or other carrier eg wireless with appropriate video and media selected based on the above and delivered to remote users via multicast.

Wherever the term device is used herein, the skilled person should appreciate that such reference should not be construed narrowly and any suitable device is intended and not limited to computer, for example an input device, output device, display device, mouse, keyboard, mobile phone, telephone, PDA, computer, games console or MP3 player, car, light switch, item of furniture, garment, building, electronic, electromechanical or other object or system.

Hence, it can be seen that a mechanism whereby information relating to a user or generally a conscious system can be accessed and used as parameters for search query or other operations to retrieve "Profiled Content" for a user without the Personal Information of the user or conscious system being disclosed.

The parameters can be derived from a plurality of sources of different types, for example but not limited to survey results, internet browsing habits, physical-psycho-social demographics, biometrics, location and/or device information. The skilled person will appreciate that parameters can be derived using any suitable technique appropriate for a given circumstance and the example parameters and derivation techniques recited above, for example in Table IV, are purely for exemplary purposes only That claimed is:

1. A system for providing content to at least one content delivery requirement entity, the system comprising:
at least one processor; and
a memory storing instructions executable by the at least one processor to perform operations comprising:

storing first entity information that enables at least one content intermediary entity to:
source first content from at least one source of content, and
deliver the first content to the at least one content delivery requirement entity, wherein the at least one content intermediary entity is arranged to process requests for sourcing data, and wherein a recipient of the data to be sourced is anonymous with respect to the at least one content intermediary entity;
transmitting, as a private communication, to the at least one content delivery requirement entity and in response to a request for the first content that identifies a first entity to a trusted holder of first profile data, a token configured for use in a content delivery software application running on the at least one content delivery requirement entity; and
communicating, over a network to the at least one content intermediary entity, the token and the first entity information;
wherein the system is arranged to provide for private communication to at least one first entity device or to the at least one content delivery requirement entity.

2. The system of claim 1, wherein the token and first entity information are communicated with the transmission of the token.

3. The system of claim 1, wherein the at least one content intermediary entity is configured to match the communicated token to the token received from the at least one content delivery requirement entity.

4. The system of claim 1, wherein the first content is configured for display at the at least one content delivery requirement entity.

5. The system of claim 4, wherein the first content recommends or provides connections to one or more people.

6. The system of claim 1, wherein the first profile data comprises at least one profile element having a value indicating relating to a personality, personality profile or personality type of the first entity.

7. The system of claim 1, wherein the first profile data comprises at least one profile element having a value indicating a symptom or medical condition.

8. The system of claim 7, wherein:
the first profile data further comprises biometric information; and
the first content is sourced based on the profile data.

9. The system of claim 4, wherein the at least one content delivery requirement entity is associated with a building.

10. The system of claim 9, wherein:
the first profile data further comprises biometric information; and
the first content is sourced based on the biometric information.

11. The system of claim 4, wherein the at least one content delivery requirement entity is a vehicle.

12. The system of claim 11, wherein:
the first profile data comprises biometric information; and
the first content is sourced based on the biometric information.

13. The system of claim 4, wherein the at least one content delivery requirement entity is a garment.

14. The system of claim 13, wherein:
the first profile data comprises biometric information; and
the first content is sourced based on the biometric information.

15. The system of claim 4, wherein the at least one content delivery requirement entity is at least one of a device, a mouse, a keyboard, a telephone, a personal digital assistant (PDA), a computer, a game console, a music player, a light switch, an item of furniture, an electronic device, or an electromechanical device or a device comprising a display.

16. The system of claim 15, wherein:
the first profile data comprises biometric information; and
the first content is sourced based on the biometric information.

17. The system of claim 1, wherein:
the first profile data comprises biometric information; and
the first content is sourced based on the biometric information.

18. The system of claim 1, wherein the first content comprises a plurality of segments.

19. The system of claim 18, wherein at least one of the segments is either unique to the at least one content delivery requirement entity or delivered to the at least one content delivery requirement entity and a second device.

20. The system of claim 1, wherein:
the first entity information is associated with a first content delivery requirement entity;
and the operations further comprise:
storing second entity information associated with a second content delivery requirement entity, the second entity information enabling the at least one content intermediary entity to:
source second content from the source of content,
deliver the second content to a second content delivery requirement entity, and
simultaneously videocast a first communications stream comprising the first content to the first content delivery requirement entity and a second communications stream comprising the second content to the second content delivery requirement entity; and
communicating, over the network to the at least one content intermediary entity, the second entity information.

21. The system of claim 20, wherein the first content comprises a plurality of first segments and the second content comprises a plurality of second segments.

22. The system of claim 21, wherein at least one of the first or second segments may be dynamically changed based on a change to the first profile data or second profile data associated with the second entity information.

23. The system of claim 21, wherein:
the first entity information or second entity information comprises biometric information; and
at least one of the first or second segments is based on the biometric information.

24. The system of claim 1, wherein the first profile data is associated with at least one of a group, community, or city.

25. The system of claim 1, wherein a change in at least part of the first profile data triggers the request for the first content.

26. The system of claim 1, wherein the system is configured to determine a demographic grouping based on the first profile data and second profile data associated with a second entity, the first profile data being associated with the first entity.

27. The system of claim 1, wherein the first profile data is associated with the first entity and comprises data based on information aggregated from second profile data of at least a second entity.

28. The system of claim 1, wherein the first profile data comprises at least one function.

29. The system of claim 1, wherein the profile data comprises at least one of executable data, a script, a formula, or software.

30. The system of claim 1, wherein the first profile data comprises at least one profile element having a value indicating an attribute of the first entity.

31. The system of claim 30, wherein the attribute is a performance goal of the first entity.

32. The system of claim 30, wherein the first content is determined based on the attribute of the first entity.

33. The system of claim 30, wherein the attribute comprises at least one of a purpose, vision, value, intention, objective, or project of the first entity.

34. The system of claim 30, wherein the attribute relates to at least one of a principle or value of the first entity.

35. The system of claim 30, wherein the attribute indicates a purpose of achieving at least one of an improvement, performance, or success of the first entity.

36. The system of claim 30, wherein the at least one profile element comprises at least one of executable data, a script, a formula, or software executable by at least one of the at least one processor or a client of a web service provided by the system.

37. The system of claim 36, wherein the at least one of executable data, a script, a formula, or software is used to derive contents of an access control group.

38. The system of claim 37, wherein the access control group contains at least one of executable data, a script, or a software program, which may be executed by at least one of the system or the at least one content intermediary entity.

39. The system of claim 30, wherein the attribute is a conduct attribute comprising at least one of a habitual thought pattern of the first entity, a social state of the first entity, a psychological state of the first entity, or a physiological state of the first entity.

40. The system of claim 39, wherein the conduct attribute is determined by assessing the first entity, the first entity being an individual or a group.

41. The system of claim 30, wherein the attribute corresponds to data from a model for understanding at least one of a social, psychological or physiological state of the first entity.

42. The system of claim 41, wherein the test measures biometric information associated with the conduct attribute.

43. The system of claim 42, wherein:
the test yields a positive biometric response of the first entity to at least one of a product or service; and
the first content is determined based on the positive biometric response.

44. The system of claim 43, wherein the biometric information comprises at least one of: a pulse rate, an electrocardiogram (ECG) result, an electroencephalogram (EEG) result, an electromyography (EMG) result, a galvanic skin response, a brain signal, a respiration rate, a body temperature, a facial movement, a facial expression, or a blood pressure measurement.

45. The system of claim 1, wherein the first profile data comprises biometric information, the biometric information comprising at least one of: a pulse rate, an electrocardiogram (ECG) result, an electroencephalogram (EEG) result, an electromyography (EMG) result, a galvanic skin response, a brain signal, a respiration rate, a body temperature, a facial movement, a facial expression, or a blood pressure measurement.

46. The system of claim 1, wherein the first profile data is based on linguistic information from a current focus of attention of the first entity.

47. The system of claim 46, wherein the linguistic information comprises a proper noun.

48. The system of claim 1, wherein the first content is associated with at least one of: an advertisement, a person, an organization, a community, a place, a document, a product, a service, a website, or a webpage.

49. The system of claim 48, wherein the first content comprises video content.

50. A non-transitory computer readable medium including instructions that, when executed by at least one processor, cause the at least one processor to perform operations for providing content to at least one content delivery requirement entity, the operations comprising:
storing entity information that enables at least one content intermediary entity to:
source content from a source of content, and
deliver the content to the at least one content delivery requirement entity, wherein the at least one content intermediary entity is arranged to process requests for sourcing data, and wherein a recipient of the data to be sourced is anonymous with respect to the at least one content intermediary entity, wherein the at least one content delivery requirement entity is arranged to provide for private communication or the recipient is associated with a first entity device arranged to provide for private communication;
transmitting, as a private communication, to the at least one content delivery requirement entity and in response to a request for the first content that identifies an entity to a trusted holder of profile data, a token configured for use in a content delivery software application running on the at least one content delivery requirement entity; and
communicating, over a network to the at least one content intermediary entity, the token and the first entity information.

51. A computer-implemented method for providing content to at least one content delivery requirement entity, the method comprising:
storing entity information that enables at least one content intermediary entity to:
source content from a source of content, and
deliver the content to the at least one content delivery requirement entity, wherein the at least one content intermediary entity is arranged to process requests for sourcing data, and wherein a recipient of the data to be sourced is anonymous with respect to the at least one content intermediary entity, wherein the at least one content delivery requirement entity is arranged to provide for private communication or the recipient is associated with a first entity device arranged to provide for private communication;
transmitting, as a private communication, to the at least one content delivery requirement entity and in response to a request for the first content that identifies an entity to a trusted holder of profile data, a token configured for use in a content delivery software application running on the at least one content delivery requirement entity; and
communicating, over a network to the at least one content intermediary entity, the token and the first entity information.

* * * * *